US008454892B1

(12) United States Patent
Rychwalski et al.

(10) Patent No.: US 8,454,892 B1
(45) Date of Patent: Jun. 4, 2013

(54) CHEMICAL AGENT DETECTION SYSTEM FOR FLUID MEDIA

(75) Inventors: Edward M. Rychwalski, Abingdon, MD (US); Stephen J. Comaty, Belcamp, MD (US); James A. Genovese, Street, MD (US); Patrick Nolan, Havre de Grace, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 295 days.

(21) Appl. No.: 12/905,729

(22) Filed: Oct. 15, 2010

(51) Int. Cl.
*G01N 31/00* (2006.01)
(52) U.S. Cl.
USPC ............... 422/68.1; 422/69; 422/70; 422/527
(58) Field of Classification Search
USPC ................... 422/68.1, 69, 70, 527; 436/177, 436/178; 210/656, 660, 661, 662
See application file for complete search history.

(56) References Cited

PUBLICATIONS

Guilbot, P. et al. "Rapid on-line sampler-injector: a reliable tool for HT-HP sampling and on-line GC analysis." Analysis (2000) 28 426-431.*
Smith, Philip A. et al. "Detection of gas-phase chemical warfare agents using field-portable gas chromatorgraphy-mass spectrometry systems: instrument and sampling strategy considerations." Trends in Analytical Chemistry (2004) 23 296-306.*

* cited by examiner

*Primary Examiner* — Yelena G Gakh
*Assistant Examiner* — Christopher A Hixson
(74) *Attorney, Agent, or Firm* — Ulysses John Biffoni

(57) ABSTRACT

A chemical agent detection system is provided that includes a fluid sampling collector suitable for the collecting, concentrating, filtering and storing of chemical agents. Preferably a solid phase extraction syringe is coupled to an adaptor via an injection port. The adaptor forms an outer surface of a sample containment reservoir that allows the fluid sampling collector to associate with a chemical agent detector such as the M256A2 chemical agent detector. The inventive chemical agent detection system allows rapid, low level on-site detection of chemical agents such as nerve agents in fluid media.

14 Claims, 3 Drawing Sheets

US 8,454,892 B1

CHEMICAL AGENT DETECTION SYSTEM FOR FLUID MEDIA

GOVERNMENT INTEREST

The invention described herein may be manufactured, used and licensed by or for the U.S. Government.

FIELD OF THE INVENTION

The invention relates in general to a process and apparatus for the detection of chemical agents in fluid media, and in particular to collecting samples and concentrating chemical agents contained therein for subsequent detection on a chemical agent detector.

BACKGROUND OF THE INVENTION

Due to the worldwide spread of chemical arms, there is an ever-expanding danger of exposure to chemical warfare agents. Water sources are vulnerable to contamination by chemical warfare agents (CWA) and other hazardous materials. The U.S. Army M272 Chemical Agent Water Testing Kit represents a conventional kit that analyzes water for the presence of nerve agents but is insufficient for detection under many circumstances. For example, in hot arid climates where water consumption significantly exceeds 5 liters per day, the binary pass-fail characteristic of the M272 test kit for nerve agents is inadequate for determining potability since the allowable concentration of agent decreases proportionately with the increase of daily water consumption demands such that the maximum allowable daily dose of agent remains constant. For example, the allowable concentration of nerve agent in potable water is 20 ppb (0.02 mg/L) for temperate climate consumption of 5 liters per day. In hot arid climates the maximum allowable concentration is reduced to 5 ppb (0.005 mg/L) as water consumption could reach 15 liters per day. Thus, a CWA test kit with high sensitivity is an urgent need not only for military personnel in the field, but also civilians and agricultural operations in close proximity to a contaminated water source.

Another common problem with existing field test kits is that testing is labor intensive. For example, the M272 kit has small glass tubes fitted to a beaker using rubber fittings. To run a test, three glass capillary tubes are required, as well as the addition of three foil packets of chemicals to the glass beaker at separate times. The M272 kit produces color changes indicative of a positive or negative response for a test agent. At times, these color changes can be ambiguous and occur in a small area on a rounded surface of a capillary tube side wall potentially leading to the incorrect reading of results. Test operations performed while wearing protective equipment are especially prone to error. Protective gloves are also vulnerable to being breached by the need to handle and break glass micro capillary tubes that produce glass shards, thereby risking exposing a wearer to the agent.

Thus, there is a need for a sensitive, reproducible and field ready fluid test kit that can be used to detect chemically hazardous agents such as chemical nerve agents, other CWAs, pesticides, herbicides, or other environmental hazardous materials.

SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

The United States military has expended great time and effort in creating improvements for the M272 water hazard sampling and detection system. The current inventors have surprisingly discovered that inventive adaptations- to an existing M256A2 chemical agent detection kit provide unexpected and significant improvements over the functions of either the M256A2 or the M272 test kits alone. The inventive chemical agent detection system provides a versatile handheld detector that can be used by all soldiers and emergency responders as well as field investigating agents. The inventive system includes a fluid sampling collector for use with a chemical agent detector. A fluid sampling collector includes a sample containment reservoir that is movably attachable to a chemical agent detector and also removably attachable to an adaptor that has an injection port. A fluid sampling container associates with the injection port whereby eluate from the sampling container is transferred to the chemical agent detector through the sample containment reservoir. In a preferred embodiment the chemical agent detector is the M256A2 chemical agent detector.

An inventive adaptor is attachable to the sample containment reservoir preferably by a slot in the reservoir. Thus, fitting the adaptor into the sample containment reservoir may provide a seal preventing unwanted fluid escape. The positioning of the adaptor preferably aligns the eluate in the center of a detection region in a chemical agent detector. The adaptor also has one or more channels for associating with the sample containment reservoir. The channels optionally fit into the slot on the sample containment reservoir guiding positioning of the adaptor therein.

A fluid sampling container preferably contains a solid phase media. The solid phase media can be alkyl-bonded silica wherein the alkyl chain is a $C_{18}$ alkyl chain or alternatively a Hydrophilic-Lipophilic Balance (HLB) cartridge. In a preferred embodiment the sampling container is a solid phase extraction (SPE) syringe. Numerous methods for removably fitting a sampling container to an injection port on an adaptor are operable herein but are preferably selected from the group including a press fitting, a Luer-Lok coupling, or a needle puncture. The injection port on an adaptor optionally is an orifice that includes a breachable resealing membrane disposed therein.

A fluid is optionally an eluate. An eluate optionally contains an eluted chemical illustratively a pesticide, an herbicide, insecticide, drug, chemical warfare agent, radioactive agent, a biological sample, other chemical, or combinations thereof. Preferably the eluted chemical agent is a CWA. CWAs preferably detected by the subject invention include blister agents, blood agents, and nerve agents. Nerve agents particularly preferred include VX, tabun (GA), sarin (GB), and soman (GD).

Also included is an inventive method of detecting the presence of a chemical agent in a fluid medium whereby a chemical agent is adsorbed to a solid phase medium housed in a fluid sampling container. The inventive method includes eluting the chemical agent onto a chemical agent detector through an adaptor that is removably connected to a sample containment reservoir and activating the chemical agent detector to detect the presence or the absence of a chemical agent. Preferably the chemical agent detector is the M256A2 chemical agent detector. Chemical agents preferably detected by the inventive method include pesticides, herbicides, insecticides, drugs, chemical warfare agents, biological samples, radioactive materials, toxic or nontoxic chemicals. Preferably, the agent is a CWA such as blister agents, blood agents, and nerve agents. Illustrative nerve agents include VX, tabun, sarin, and soman.

DETAILED DESCRIPTION OF THE PREFERRED EMBODIMENTS

The inventive apparatus and method provide a field analytical method and system for the determination of chemical agents in fluid media such as drinking water. As such, the invention provides an unexpected solution to the prior art lack of sensitivity, ease of use, and safety of use problems. A novel fluid sampling collector is provided that is useful in field expedient sampling of fluidic media, particularly when employed as part of the M256A2 chemical agent detection kit. As such, the present invention has utility for collecting, concentrating, and detecting chemical agents in fluidic media.

The current invention provides a versatile handheld detector that can be used in the field by sampling personnel. The inventive detector preferably employs a solid phase extraction method that effectively is used to sample, filter, concentrate, and deliver fluid sample hazards for rapid, high-sensitivity detection. The current invention allows all detection chemicals and reactants to be present on a single card and uses simple colorimetric chemistry for the detection of chemical agents.

Figure 1:
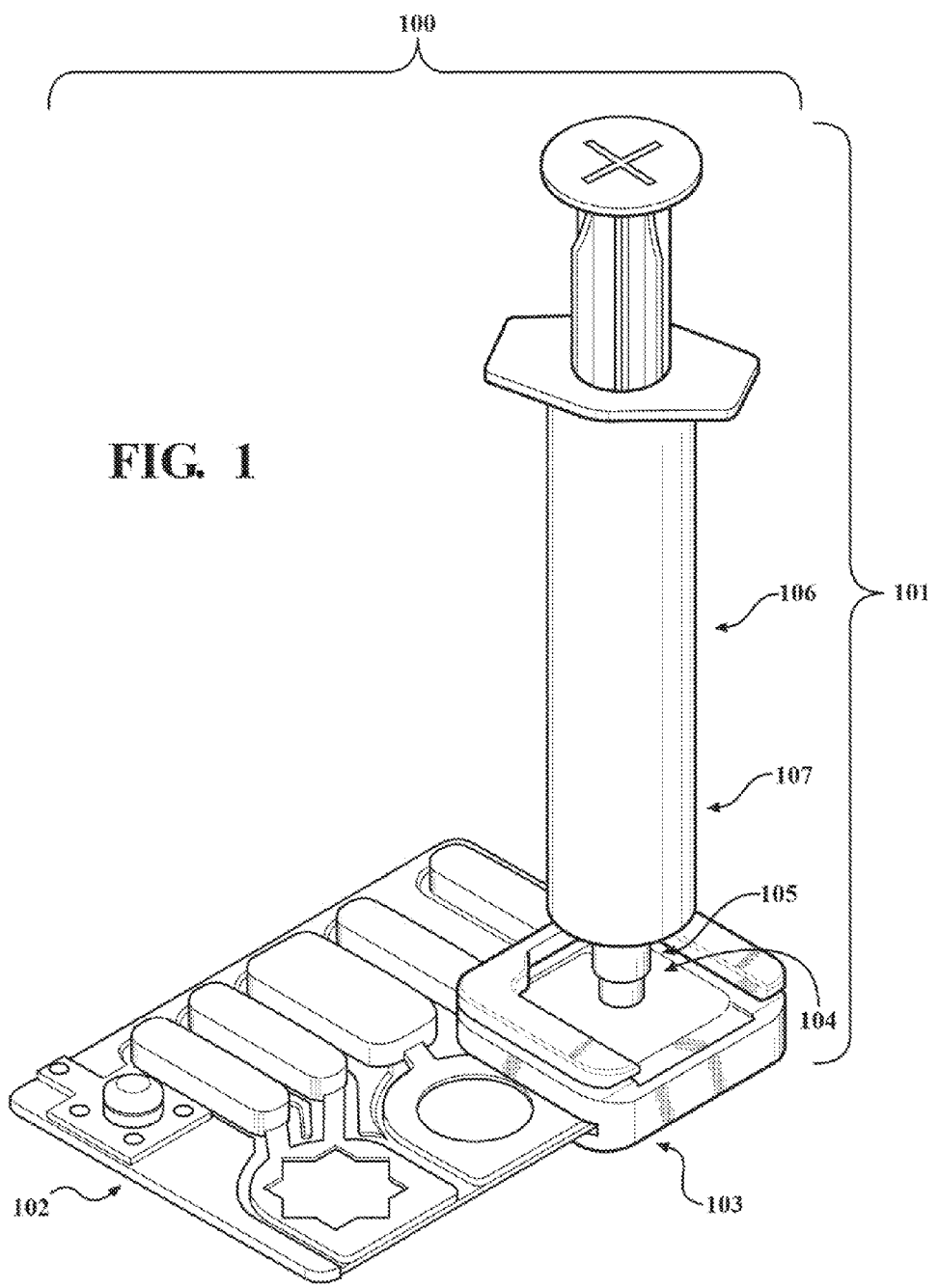
FIG. 1 is a perspective partially transparent view of an inventive chemical agent detection system including a chemical agent detector and a fluid sampling collector.

As seen in FIG. 1, an inventive chemical agent detection system is shown generally at 100 and includes a fluid sampling container 101 that movably mates with a chemical agent detector 102. The fluid sampling container 101 is optionally removable. The chemical agent detector depicted in FIG. 1 is the M256A2 chemical agent detector, but it is appreciated that other chemical agent detectors are similarly operable. Optionally, a chemical agent detector contains collecting media that, is later processed for chemical detection. Optionally, a chemical agent detector is a gas chromatograph, liquid chromatograph, or a mass spectrometer alone, combined, or coupled to a liquid chromatography system.

The fluid sampling detector 101 is preferably formed of several components including a sample containment reservoir 103 that movably attaches to a chemical agent detector 102 allowing sample to be deposited in more than one location on the chemical agent detector 102. An adaptor 104 removably attaches to the sample containment reservoir 103 to form a containment chamber. An adaptor 104 contains an injection port 105 that removably attaches to a fluid sampling container 106. The fluid sampling detector 101 is used to sample fluidic environmental materials and collect chemicals of detection interest therein. A fluid obtained by eluting a chemical agent from the solid phase media, for example, in the fluid sampling container is transferred from the fluid sampling container 106 through the injection port 105 and adaptor 104 into the chamber within the sample containment reservoir 103. The combination of the fluid sampling container 101 and the chemical agent detector 102 provides expanded capability to detect chemical agents within fluidic media such as nerve agents or pesticides.

Figure 2:
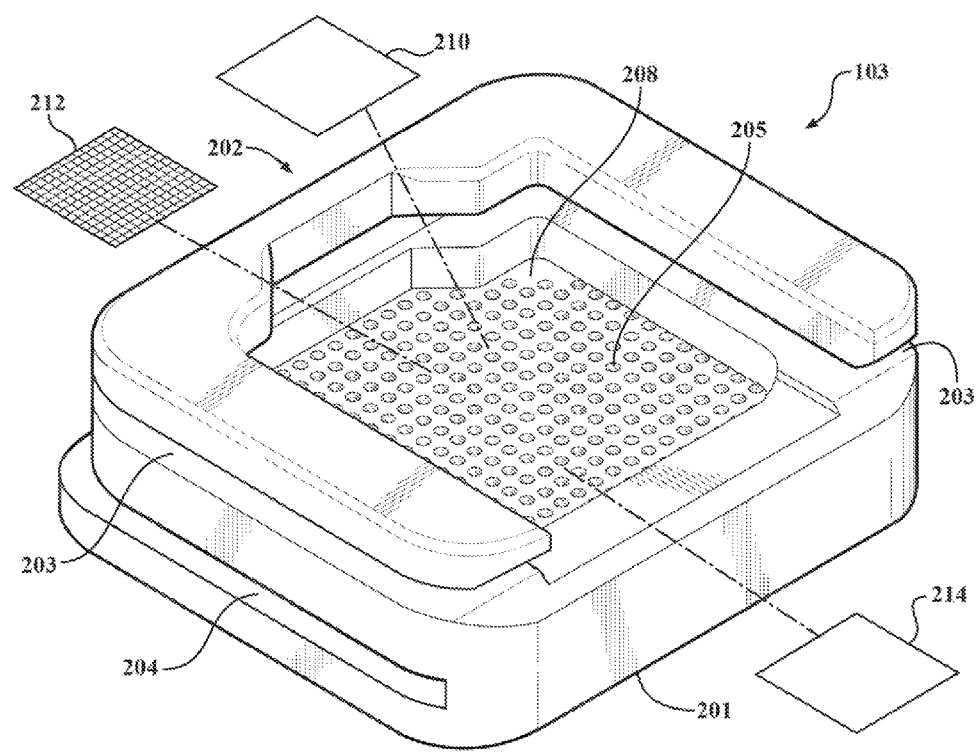
FIG. 2 is a perspective view of a sample containment reservoir operative with the system of FIG. 1.

FIG. 2 depicts a preferred embodiment of a sample containment reservoir 103. The sample containment reservoir 103 includes a first side 201 that establishes the base of the sample containment reservoir. A second side 202 is preferably an open side suitably shaped to receive an adaptor for the formation of a closed reservoir system. Proximate to the second side 202 is a first slot depicted at 203 of sufficient shape and size to provide a friction fit with an adaptor. Below a first slot 203 is a second slot 204 that is operable for receiving a chemical agent detector such that the chemical agent detector is capable of being moved through the second slot 204 to allow the depositing of fluidic samples onto various portions of the chemical agent detector. Intermediate between the first slot 203 and the second slot 204 is optionally an intermediate layer 205. The intermediate layer 205 optionally has perforations 208 so that fluid being transferred into the sample containment reservoir 103 passes through the perforations 208 and onto one or more positions of a chemical agent detector as per FIG. 1. An intermediate layer 205 optionally contains a filtering system 210, such as glass fiber filters, with or without binder resin; quartz fiber filters; polypropylene; polyethylene; other polymeric filters, nylon; cellulosic filters, or particulate filtration materials. Filtering materials suitable for use in a filtering system 210 are preferably nonreactive with eluent solvents or the agents sampled. Optionally, an intermediate layer filter system 210 is a size exclusion filter allowing for a further purification and separation step following elution from a fluid sampling container. Optionally, a filter membrane 212 is layered on top of an intermediate layer 205 such that any eluate must pass through a filtration layer prior to being deposited on a chemical agent detector. In addition to those listed previously, ultrafiltration discs such as cellulose membranes or polyether sulfone membranes that are suitable for molecular weight separations are operable in an intermediate filtering system 210. Alternatively, a filtration disc or membrane may contain a selectively binding material that may or may not filter out known or unknown contaminants, thus, enhancing the detection capability of the inventive system.

In a preferred embodiment the sample containment reservoir 103 is formed as a structure constructed, of materials that are not degraded by either thermal heating of the eluate or solvent materials that are passed through the sample containment reservoir. Suitable materials illustratively include stainless steel, hardened polymeric compositions, plastic polymers, metals, metal alloys, composites, and the like, with selection of the appropriate material determinable by those skilled in the art through ordinary experimentation in light of the disclosure herein, including considerations of interfering chemical breakdown products or other interfering materials or processes. Variations and subsequent changes to the sample containment reservoir 103 may include optimized designs or redesigns for production and marketing such as for example and without limitation, changes in the size or geometry of the sample compartment reservoir 103 to enhance performance, production rates, compatibility, convenience, etc. with designs, adjustments, or changes preferably completed to maximize diffusion or transfer of sample eluate to allow a more rapid time period or improved detection accuracy by the detector. Preferably, the sample containment reservoir 103 has an area from 1.5 $cm^2$ to 12.0 $cm^2$, more preferably from 6 $cm^2$ to 10 $cm^2$ with the sample containment reservoir 103 having a receptacle or containment volume of from 0.1 $cm^3$ to 32 $cm^3$, more preferably from 1 $cm^3$ to 6 $cm^3$.

While the aforementioned shape and dimensions of a sample containment reservoir are optimized for a card or other solid substrate used as a chemical agent detector, the sample containment reservoir is not limited to these sizes or shapes. For example a sample containment reservoir can be spherical, cylindrical, trapezoidal, or other shapes, or combinations of more than one overall shape. Optionally, internal shaping need not match external shaping. Illustratively, a sample containment reservoir can be rectangular in its outer dimensions and have an internal space that is circular or cylindrical. Shape and size considerations are dependent on the type of chemical agent detector intended to be coupled to the sample containment reservoir, the portability or packability of the system, the presence or absence of intermediate filters or media present in the sample containment reservoir or other considerations that will be apparent to one of ordinary skill in the art during the use or design of experiments with the inventive system.

A sample containment reservoir 103 optionally includes a heating element 214 such as that described in U.S. Pat. No. 7,036,388. A heating element is optionally used to adjust the temperature or other parameter of the sample as it is deposited onto the chemical agent detector to improve or otherwise adjust the detection capabilities of an inventive system. Additional structural and component considerations of an inventive sample containment reservoir can be found in U.S. Pat. No. 7,036,388, the contents of which are incorporated herein by reference.

As shown in FIG. 1, a sample containment reservoir 103 movably attaches to a chemical agent detector 102 such that multiple positions on the chemical agent detector may be exposed to an eluate or other sample transferred through a sample containment reservoir. Preferably a chemical agent detector is the M256A2 chemical agent detection kit, including its M256A1 chemical detector that is described in Department of the Army Technical Manual, TM3-6665-307-10, titled "A Operator's Manual for Chemical Agent Detector Kit, M256 (6665-01-016-8399) and M256A1 (6665-01-133-4964), September 1985." Additional disclosures include the Army Technical Manual TM3-6665-331-10, the M8 chemical agent detection paper described in army supply bulletin SB3-6665-2, and U.S. Army Chemical, Research, Development and Engineering Center, Technical Report CRDEC-SP-049 entitled "Catalog of Chemicals Contained in Chemical Detector, Decontaminating, and Training Kits" (Peter Spaeth July 1992). The disclosure of each of these references is hereby incorporated herein by reference in their entirety as descriptive of the considerations and operation of a preferred chemical agent detector operable in the present invention.

Figure 3:
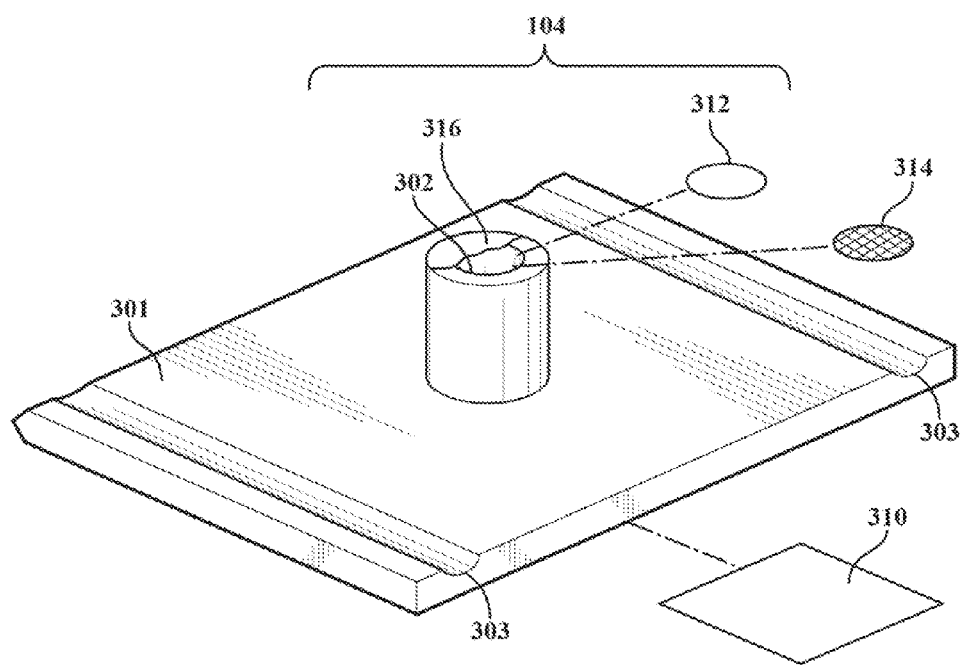
FIG. 3 is a perspective view of an adaptor operative with the system of FIG. 1.

An inventive adaptor component selectively securing with a sample containment reservoir 103 is shown generally at 104 in FIG. 3. An adaptor 104 includes a plate structure 301 that optionally has one or more grooves 303 constructed therein. The grooves are complementary to a sample containment reservoir by sliding into the slot depicted at 203 in FIG. 2, such as to form a Luer fitting. This association optionally provides a sufficient seal such that fluid does not escape the sample containment reservoir 103 when an adaptor 104 is attached thereto. The system 100 increases the level of safety for use of a chemical agent detection system and further allows for a pressure transfer of eluate from a sampling container through an optional membrane or filter and onto a chemical agent detector. An adaptor 104 optionally has one or more sealing mechanisms 310 such as rubber strips or rings that surround the periphery or other location on an adaptor 104. Alternatively, rubber gaskets or other sealing systems are associated with a sample containment reservoir whereby association with an adaptor 104 also allows for a fluidic seal. An inventive adaptor 104 further has an injection port 302 situated on one surface. An injection port 302 is preferably shaped and sized to allow for a removable association with a sampling container 101.

An adaptor 104 is preferably made from any material used in the construction of a sample containment reservoir 103.

The dimensions of an adaptor 104 allow the adaptor 104 to associate, easily with a sample containment reservoir 103 and preferably does not obstruct the view or use of a chemical agent detector 103. Principal dimensions include the thickness of an adaptor 104 correlating with the dimensions of the slot on a chemical agent reservoir 103 that the adaptor slides into. Width and length dimensions are preferably complementary to width and length dimensions of a sample containment, reservoir. Most preferably, an adaptor 104 is dimensioned as to completely encase a reservoir within the sample containment reservoir 103 by allowing for a completely enclosed cubically dimensioned space. As such the length and width of an adaptor 104 is preferably at least the length and width of the internal dimensions of a sample containment reservoir 103. More preferably, the length and width of an adaptor 104 extends to the outer edges of a sample containment reservoir 103 when an adaptor 104 is positioned within the slots of a sample containment reservoir 103.

In one embodiment an adaptor 104 is integrated with the sample containment reservoir 103. In this embodiment, a single piece system is formed so as to allow for syringe pressure injection applications, as well as improved cleanliness in shipping, handling or usage.

An injection port 302 is preferably centrally located on an adaptor 104. It is appreciated that other locations on the adaptor 104 for an injection port 302 are similarly operable. An injection port 302 is preferably of sufficient size in diameter and height so as to allow a sufficient seal between an adaptor 104 and a fluid sampling container 101 such that fluid does not leak from the seal when being injected from the sampling container into a sample containment reservoir 103. An injection port 302 is optionally an orifice in the surface of an adaptor 104 that is transposed by a membrane 312. In this embodiment breach of the membrane such as by a needle allows transfer of the sample fluid into a sample containment reservoir 103. Materials operable for a membrane 312 include rubber or plastics or any other material that may be breachable and resealed following removal of a sample injector such as a needle. Numerous materials for a membrane are known in the art and useful herein.

Preferably an injection port 302 allows for a friction fitting between an adaptor and a fluid sampling container. Numerous fittings are operable herein, illustratively including a press fitting, a Luer-Lok coupling, and the like. In a preferred embodiment a Luer-Lok coupling is used to attach an adaptor to a sample containment reservoir via the injection port. An injection port 302 optionally contains a filter 314 as a membrane or media therein that allows for additional purification or separation of chemical agents in an eluate from a fluid sampling container 103. A filter 314 operable herein as a membrane in an injection port are similar to those operable for use in a sample containment reservoir.

In one embodiment an injection port 302 contains a filter 314 seal that when an adaptor 104 is associated with a sample containment reservoir 103, a sealed chamber is formed to improve sterilization and prevent other contaminants from entering a sample containment reservoir during shipping or other handling. Alternatively, an injection port 302 is covered at either end or within the port by a breachable seal 316 of foil or other material that allows clean handling and can be easily opened by a user prior to sample injection.

Optionally, an adaptor 104 has more than one injection port 302. Multiple injection ports may be operable for injection or insertion of more than one solvent or other fluids into a sample containment reservoir 103. Illustratively, two injection ports are present on an adaptor 104. This embodiment allows multiple fluids such as an eluate and a reactive fluid to be simultaneously injected into a sample containment reservoir 103 allowing the reservoir to act as a reaction chamber for enhancing the detection of a chemical agent in an eluate.

A fluid sampling container 101 is any container capable of housing fluid within a chamber. Numerous types of fluid sampling containers are operable with the present invention illustratively including a syringe, column, pipette, Eppendorf type tube or other sealable tube, and the like. In a preferred embodiment, a fluid sampling container is a syringe. A syringe is preferably coupled to an adaptor via the injection port through a Luer-Lok type association. It is appreciated that other types of fittings are similarly operable such as a press fitting.

A fluid sampling container 101 preferably contains a solid phase media 107. Solid phase media 107 is generally positioned with one or more fits or packing materials so as to hold the solid phase media in position when sample is drawn through the media or eluant/eluate is pushed out. A solid phase extraction (SPE) syringe is most preferred as a fluid sampling container. SPE syringes are available from commercial suppliers such as Sigma Aldrich Company (St. Louis, Mo.). In a most preferred embodiment, SPE material is positioned within an SPE syringe between two fits or packing material. Frits or packing material are preferably polyethylene, but other materials such as Teflon or stainless steel are similarly suitable. Frits are available with numerous pore sizes, but the pores should be small enough such that the frits can retain the SPE material at a position within the syringe so that the material does not leave the syringe upon elution. Preferably a 20 micrometer pore size is present in a frit.

A SPE syringe or other fluid sampling container is preferably formed of a material that will not react with either the fluid or other material being sampled, solvents, or other materials used for detecting a chemical agent. Numerous materials are available for the formation of a fluid sampling container illustratively including polypropylene, polyethylene, glass, or other materials known in the art.

Several types of solid phase extraction media are operable herein. The choice of solid phase extraction media will be readily apparent to those of ordinary skill in the art depending on the type of chemical agent to be detected and its chemical properties and characteristics. In a preferred embodiment, solid phase extraction media is an alkyl bonded silica. More preferably the alkyl chain is a $C_{18}$ alkyl chain or HLB packing. $C_{18}$ alkyl chains are most useful for reversed phase extraction of nonpolar to moderately polar compounds. It is appreciated that other SPE materials for other types of extraction are similarly suitable in the invention. For example, normal phase SPE media is also available. In addition, ion exchange such as anion exchange SPE media or cation exchange SPE media is also useful herein as well as size exclusion chromatography, affinity chromatography, or other chromatographic separation techniques known in the art. Particle size of the packing material and type of packing material will depend on the type of extraction procedures used in the fluid sampling container. For example, silica-based packing material optionally has 40 micrometer particles with 60 angstrom pores.

An eluant operable for eluting a chemical agent from solid phase extraction media is preferably tailored to the media used. Illustratively, an alkyl bonded media is eluted with an eluant containing methanol or methylene chloride. Affinity chromatography is illustratively eluted with an eluant that disrupts the interactions with the ligand bonding the chemical agent of interest. Size exclusion chromatography is preferably performed with an eluant that is chemically inert with respect to the chemical agent for detection. Illustrative examples of eluant components include: methanol; ethanol; isopropyl alcohol (IPA); dichloromethane (DCM); hexane; heptane; acetic acid; salts; buffers illustratively, HEPES, Tris, or phosphate; water, or combinations thereof.

Numerous bonding agents such as octadecyl bonding agents are operable to bind and associate with chemicals within a sample. Other examples illustratively include octyl agents, butyl dimethyl agents, phenyl, hydrophobic surfaces, cyanopropyl, diol, aminopropyl, quaternary amine, sulfonic acid, carboxylic acid, or no bonding materials. For affinity chromatography such as for the detection of biological agents, numerous bonding materials are available illustratively including antibodies, nucleic acids, aptamers, lipids, and the like.

An octadecyl bonding agent such as a $C_{18}$ bonding agent is preferred. This material is capable of reverse phase extraction of a wide variety of chemical agents that may or may not be present in a fluid media. Illustrative chemical agents include antibiotics, barbiturates, benzodiazepines, caffeine, drugs, dyes, essential oils, fat-soluble vitamins, fungicides, herbicides, pesticides, hydrocarbons, parabens, phenols, phthalate esters, steroids, surfactants, theophylline, water-soluble vitamins, chemical warfare agents, nerve agents, hazardous or nonhazardous industrial chemicals, and the like. In this embodiment, any one or combinations of the aforementioned materials or chemicals is detected by the inventive system. It is appreciated that this is an incomplete list and numerous other chemical agents can be detected by the inventive system.

The inventive chemical agent detection system is suitable for analyzing fluidic as well as solid, or vapor samples. Preferably fluidic samples such as water or other environmental fluids illustratively including blood, plasma, solubilized tissue, industrial solvents, or other fluid are useful. Alternatively, a solid environmental or other sample is analyzed by the inventive chemical agent detection system. Solid samples are preferably dissolved, solubilized via soaps, surfactants, cosurfactants, detergents or placed in a fluidic colloidal suspension and agitated so that chemical agents can be transferred to the detector for subsequent detection. In a preferred embodiment, a sample and subsequently an eluted chemical agent in an eluate is a pesticide; herbicide; insecticide; drug; chemical warfare agent; biological sample such as a bacteria, virus, fungus, tissue, radioactive material or other chemical. More preferably a sample or chemical agent in an eluate is a chemical warfare agent. Chemical warfare agents are optionally blister agents, blood agents, and nerve agents. Preferred nerve agents illustratively include VX, GA, GB, and GD. Preferably a sample contains a chemical agent that is isolatable by reversed phase solid phase extraction.

Also provided is an inventive process of detecting the presence of a chemical agent in a fluid medium. The inventive process includes adsorbing a chemical agent to a solid phase media housed in a fluid sampling container. Preferably, a fluid sampling container is an SPE syringe. Using an SPE syringe, typically in a reverse phase mode optimized for the extraction of analytes from aqueous samples, a water sample, for example, is drawn up by retracting a plunger. The inventive process is similarly operable utilizing a syringe or other fluid sampling container in the absence of a sorbent packing or other solid phase extraction media.

A fluid sample is illustratively passed over SPE media to bind hazardous materials from the fluid on the solid phase media. Chemical agents present in the fluid media, such as water, are bound by and retained by the SPE media. Several sampling/deluge cycles allow a larger amount of CWA analytes to be gathered into the solid phase sorbent packing thereby increasing the CWA concentration and resulting in enhanced detection sensitivity. These procedures also optionally filter out unwanted particulates from the fluidic sample, reducing turbidity-based interferences. Particulate materials containing diatomaceous earth, humic and fulvic compounds that may complex the analyte of interest can also be retained by the packing material, frit, SPE bed or other filter contained within the fluid sampling container. The retained fluid-borne particulate materials within the packing material, frit or SPE bed can later be extracted for detection through elution via an appropriate solvent.

A primary advantage of the inventive system is that remote sampling and subsequent analysis of an environmental or other sample is capable by using an inventive fluid sampling container. For example, the fluid sampling container does not have to be shipped with or otherwise associated with a chemical agent detector. A fluid sampling container is optionally shipped into the field where a sample is collected and then stored within the fluid sampling container for shipment to a central or other location for chemical agent detection. Preferably, a chemical agent detector is shipped along with a fluid sampling container so that the presence or absence of an environmental or other contaminant within a sample can be readily and immediately determined at the sample site.

Once the solid phase has been loaded with the analyte and/or additional particulate matter, the residual solution is expelled from the syringe. Should a different elution solvent be required, the elution solvent can be placed or drawn into the fluid sampling container so as to release bound chemical matter from the solid phase extraction media. When a fluid sampling container is affixed to a water sampler adaptor such as through a Luer-Lok or friction type attachment and the adaptor is associated with a sample containment reservoir on a chemical agent detector, the eluted sample is then injected onto the chemical agent detector optionally through the sample containment reservoir. Optionally, the chemical agent detector is the M256A2 chemical agent detector kit. The No. 3 ampules of the kit are broken to prepare the detection window for hazard deposition prior to elution of the chemical agent from the fluid sampling container. An appropriate solvent with high affinity for CWA analytes and that is compatible with the reagent chemistries of the chemical agent detector such as the M256A2 card is released into the solid phase extraction adsorption bed in the sampling syringe. This elutes the analyte from the solid phase. The solvent is pushed through the solid phase using the syringe plunger, carrying the dissolved CWA past and through the sample containment reservoir, and depositing sample directly onto the wetted test surface of the M256A2 detector card. It is appreciated that the sample containment reservoir is optionally appropriately sized, segregated, or unified to optionally direct sample to more than one detector window illustratively on an M256A2 detector card or other detector system. The inventive fluid sampling detector is then removed from the chemical agent detector such as the M256A2 card and the No. 5 M256A2 ampules are broken to complete the colorimetric detection test and the card is run per standard instructions. The presence or absence of a colorimetric change alerts the user as to the presence or absence of a chemical agent within the sample.

Various aspects of the present invention are illustrated by the following non-limiting examples. The examples are for illustrative purposes and are not a limitation on any practice of the present invention. It will be understood that variations and modifications can be made without departing from the spirit and scope of the invention. While the examples are generally directed to water, specifically water containing nerve agents or pesticides, a person having ordinary skill in the art recognizes that similar techniques and other techniques know in the art readily translate the examples to other fluidic or solid media or other chemical analytes.

EXAMPLES

Example 1

Detection of Nerve Agents in Water

Disposable 6 milliliter Discovery DSC-18 SPE tubes purchased from Sigma Aldrich Company (St. Louis, Mo.) are used to concentrate nerve agents from water. All organic solvents are of high purity grade. Water used for the preparation of solutions was distilled and then passed through a Millipore water purification system. The SPE syringe utilized has a polyethylene 20 micrometer frit and is comprised of polypropylene. An SPE bed weight of 1 gram is used comprised of silica gel and octadecyl bonded. Particle size is 50 micrometers with a pore size of 70 Angstroms and a surface area of 480 square meters per gram.

Solid phase extraction columns are prepared by passing 3 milliliters of methanol followed by 3 milliliters of distilled water through the columns. The SPE material is maintained moist at all times prior to the extraction procedure. Fifty milliliters of water spiked with a known amount of nerve agent is placed in a 50 milliliters reservoir. The 50 milliliter sample is drawn into the syringe by retraction of the plunger. The plunger is then pressed the opposite direction to expel the unbound material from the syringe. This binding procedure is repeated 2 times. Approximately 2 milliliters of elution solvent containing 20% methanol/80% methylene chloride (v/v) is drawn through the SPE bed. The SPE column is then attached to an injection port on an adaptor that is fitted into a chemical containment reservoir and associated with a M256A2 chemical agent detector. Eluate is transferred to the chemical agent detector by pressing the plunger on the syringe so as to move eluate from the SPE bed through the sample containment reservoir and onto the M256A2 chemical agent detector. Colorimetric detection positively identifies the presence of tabun, sarin, soman, and VX at concentrations in sample of <5 ppb.

Example 2

Detection of Organophosphorus Pesticides

Pesticides diazinon, parathion, phorate, fenchlorphus, and chlorpyrifos are prepared in reagent grade methanol at concentrations of 100 ppm. The solutions are then diluted in distilled water to obtain aqueous solutions of 50, 10, 5, 0.5, and 0.05 ppb. Each of the test solutions is bound to a $C_{18}$ high capacity SPE column as in Example 1. Two milliliters of methanol is used as the elution solution and drawn into the syringe for elution of the pesticide agents from the solid phase extraction media. Elution is performed as in Example 1 and eluted pesticides are detected by gas chromatographic analysis.

Each of the organophosphorus compounds studied is effectively removed from the sample, concentrated, and eluted into a detection system by an inventive fluid sampling collector. The detection limit of the system is below 0.005 ppb.

Example 3

Field Detection of Nerve Agents in Water

Soldiers in the field require hydration from an environmental source of unknown safety. Toxin levels must be at or below 5 μg/L for nerve, 47 μg/L mustard and 2 mg/L CN for the water to be declared safe for consumption. An inventive system is used to analyze the water. An SPE syringe with a polyethylene 20 micrometer polypropylene frit with an SPE bed weight of 1 gram comprised of silica gel and octadecyl bonded is stored in the inventive kit premoistened as per Example 1. Particle size is 50 micrometers with a pore size of 70 Angstroms and a surface area of 480 square meters per gram.

Fifty milliliters of sample water with an unknown amount of nerve agent is drawn into the syringe by retraction of the plunger. The plunger is then pressed the opposite direction to expel the unbound material from the syringe. This binding procedure is repeated 2 times. Approximately 2 milliliters of elution solvent containing 20% methanol/80% methylene chloride (v/v) is drawn through the SPE bed. The SPE column is then attached to an injection port on an adaptor that is fitted into a chemical containment reservoir and associated, with a M256A2 chemical agent detector. Eluate is transferred to the chemical agent detector by pressing the plunger on the syringe so as to move eluate from the SPE bed through the sample containment reservoir and onto the M256A2 chemical agent detector. Colorimetric detection positively identifies the absence of nerve, mustard, or CN toxins in the sample at hazardous levels such that the water is declared safe for consumption at required levels for soldier hydration.

Example 4

Detection of Nerve Agents in Water with HLB Based System

The system of Example 1 used for detection of toxins in water with the Discovery DSC-18 SPE tubes replaced by SUPEL-Select HLB SPE columns from Sigma-Aldrich, St. Louis Mo. Colorimetric detection positively identifies the presence of tabun, sarin, soman, and VX at concentrations <5 ppb.

Example 5

Field Detection of Nerve Agents in Water

The system example 4 is used for field detection as per Example 3. Colorimetric detection positively identifies the absence of nerve, mustard, or CN toxins in the sample at hazardous levels such that the water is declared safe for consumption at required levels for soldier hydration.

The invention claimed is:

1. A chemical agent detector system for liquid media, comprising:
    a chemical agent detector, wherein said chemical agent detector comprises the M256A2 chemical agent detector;
    a sample containment reservoir removably attached to said chemical agent detector;
    an adaptor having an injection port, said adaptor removably attached to said reservoir; and
    a liquid sampling container removably attached to the injection port so as to transfer a liquid successively from said container through said adaptor to said reservoir and said chemical agent detector.

2. The system of claim 1, wherein said adaptor is attached to said sample containment reservoir by a first slot in said reservoir.

3. The system of claim 1, wherein said adaptor further comprises one or more channels for associating said adaptor to said sample containment reservoir.

4. The system of claim 1, wherein said liquid sampling container includes a solid phase media.

5. The system of claim 4, wherein said solid phase media is an alkyl chain bonded silica.

6. The system of claim 5, wherein said alkyl chain is a $C_{18}$ alkyl chain or HLB.

7. The system of claim 1, wherein said sampling container is a solid, phase extraction syringe.

8. The system of claim 1, wherein said sampling container is removably attached to said injection port by a fining selected from the group consisting of: a press fitting, a Luer-Lok coupling, and a needle puncture.

9. The system of claim 1, wherein said injection port comprises an orifice with a breachable resealing membrane disposed therein.

10. The system of claim 1, wherein said fluid liquid is an eluate including a chemical agent selected from the group consisting of: a pesticide, herbicide, insecticide, drug, chemical warfare agent, biological sample, radioactive material, or a toxic chemical.

11. The system of claim 10, wherein said chemical agent is a chemical warfare agent.

12. The system of claim 11, wherein said chemical warfare agent is selected from the group consisting of: blister agents, blood agents, and nerve agents.

13. The system of claim 12, wherein said nerve agent is selected from the group consisting of VX, GA, GB, or GD.

14. The system of claim 1, wherein said sample containment reservoir and said adaptor are integrated into a single piece.

* * * * *